United States Patent
Chakravarty et al.

(10) Patent No.: US 8,960,559 B2
(45) Date of Patent: Feb. 24, 2015

(54) PACKAGED RFID PASSIVE TAG FOR SMALL SIZED DEVICE

(71) Applicant: Tata Consultancy Services Limited, Maharashtra (IN)

(72) Inventors: Tapas Chakravarty, Bangalore (IN); Deb Kumar Ghosh, Bangalore (IN); Balamuralidhar Purushothaman, Bangalore (IN)

(73) Assignee: Tata Consultancy Services Limited, Maharashtra (IN)

( * ) Notice: Subject to any disclaimer, the term of this patent is extended or adjusted under 35 U.S.C. 154(b) by 77 days.

(21) Appl. No.: 13/660,437

(22) Filed: Oct. 25, 2012

(65) Prior Publication Data

US 2013/0105585 A1  May 2, 2013

(30) Foreign Application Priority Data

Oct. 31, 2011 (IN) .......................... 3052/MUM/2011

(51) Int. Cl.
| | |
|---|---|
| *G06K 19/06* | (2006.01) |
| *G08B 13/14* | (2006.01) |
| *G06K 19/077* | (2006.01) |
| *A61B 19/00* | (2006.01) |

(52) U.S. Cl.
CPC .......... *G06K 19/07798* (2013.01); *A61B 19/44* (2013.01); *G06K 19/07752* (2013.01); *A61B 2019/448* (2013.01)
USPC ....................... 235/492; 340/572.1; 340/572.8

(58) Field of Classification Search
USPC ................. 235/492; 340/572.1, 572.5, 572.7, 340/572.8; 600/872, 873; 128/903; 29/600
See application file for complete search history.

(56) References Cited

U.S. PATENT DOCUMENTS

| | | | |
|---|---|---|---|
| 6,026,818 A | 2/2000 | Blair et al. | |
| 6,940,408 B2 * | 9/2005 | Ferguson et al. | 340/572.7 |
| 7,256,699 B2 | 8/2007 | Tethrake et al. | |
| 7,262,701 B1 * | 8/2007 | Nguyen | 340/572.7 |
| 7,336,243 B2 * | 2/2008 | Jo et al. | 343/895 |
| 7,898,420 B2 | 3/2011 | Blair et al. | |
| 2006/0241399 A1 | 10/2006 | Fabian | |
| 2008/0143535 A1 * | 6/2008 | Fischer | 340/572.7 |
| 2009/0314542 A1 * | 12/2009 | Arocha-Ferrino et al. | 174/565 |
| 2011/0181394 A1 | 7/2011 | Blair | |

FOREIGN PATENT DOCUMENTS

WO    WO 9603713 A1 *  2/1996

OTHER PUBLICATIONS

Siegel, Adam et al. "Foldable Printed Circuit Boards on Paper Substrates." Advanced Functional Materials. vol. 20, Issue 1 (2010): 28-35. Wiley Online Library. Web. Apr. 5, 2014.*

(Continued)

*Primary Examiner* — Daniel Hess
*Assistant Examiner* — Suezu Ellis
(74) *Attorney, Agent, or Firm* — Hayes Soloway PC

(57) ABSTRACT

The present application is related to a unique transponder clip comprising a UHF passive RFID tag, an encapsulation module and method of attaching the encapsulation module enclosing the transponder clip to small sized devices. In an aspect, the small sized device may be a small sized medical device such as bone screw, spine screw implants. The transponder is enclosed in the encapsulation module that is then attached to a small sized device thereby facilitating auto-identification and tracking of the small sized device.

13 Claims, 4 Drawing Sheets

(56) References Cited

OTHER PUBLICATIONS

Sirit Identity solutions "Automatic Vehicle Identification", Identity Flex Installation Manual, 900 MHz Transceiver, IDFLEX-MAN-Version 2.1, Jan. 1, 2003.
Claire Swedberg, "NEC Works on RFID Tags, Readers for Bottle Caps", RFID Journal LLC, Mar. 16, 2007, 2 pps.
Translogik "RFID Metal Tag", (available at: http://www-trans-logik.com/RFID-Solutions/rfid-tag-metal.html), accessed Oct. 18, 2012.
Edgar Sánchez-Sinencio "Radio Frequency Identification (RFID) Fundamentals and Applications", The Economist, London, Apr. 28, 2007: vol. 383, Issue 8526.

* cited by examiner

PACKAGED RFID PASSIVE TAG FOR SMALL SIZED DEVICE

FIELD OF THE INVENTION

The present invention relates to a transponder clip, an encapsulation module for holding the transponder clip and a method for activation and deactivation of the transponder clip for identifying and tracking a small sized device. More particularly the invention relates to a transponder clip including a miniature passive RFID tag, an encapsulation module for holding the transponder clip and also adapted to be attached to a small sized device or instrument and a related method for attaching the encapsulation module holding the transponder clip to the small sized device.

BACKGROUND OF THE INVENTION

Radio Frequency Identification also referred to as RFID is a well known Technology for auto-identification and tracking inventory, assets, people etc. An RFID tag consisting of a unique id is attached to a device or asset thereby providing a unique identification to the device or asset. An RFID reader is provided that interrogates the device by wirelessly reading the attached RFID tag using RF field. The RFID tag attached to the device receives the RF field from the RFID reader and returns back the unique id. This technology is implemented in a plurality of industries such as logistics and transportation, Retail, healthcare industry, and the like for improving the tracking process through traceability of each device or asset particularly small size and high volume devices such as implantable screws in a cost effective manner.

Specifically in healthcare and medical device industry the medical device OEMs (Original Equipment Manufacturers) deliver an assortment of implantable/non-implantable devices in a single kit form to individual hospitals. Such devices may be small in size and may be used in many surgical operations like spine, shoulder joint, and the like. The OEMs then bill the hospital based on actual number of such devices used. RFID tags are typically attached to each kit containing a plurality of small sized devices and such kits are tracked during outward & inwards movement in the warehouse. However, the small sized devices contained in the kit are not being tracked in such a manner as such devices are beholden to a large sized carrier kit on which a larger dimension RFID tag is placed. Moreover, tracking small size devices using a low cost RFID tag from a distance greater than at least 6-8 inches and a large number of devices simultaneously is a major issue.

Hence, there exists a need for a unique miniature passive RFID tag, a receptacle for receiving the RFID tag and a method for attaching such a receptacle to individual small sized devices for identifying and tracking a large number of small sized devices at a time thereby circumventing inadvertent loss of these devices. Further, such an arrangement needs to take into consideration various operational conditions that the small sized device may be subjected to.

Other features and advantages of the present invention will be explained in the following description of the invention having reference to the appended drawings.

OBJECTS OF THE INVENTION

It is a primary object of the invention to provide a transponder clip comprising a UHF passive RFID tag enclosed in an encapsulation module and a method for attaching the encapsulation module to a small sized device or instrument thereby enabling identification and tracking of the small sized device.

It is another object of the invention to provide a method for attaching an encapsulation module enclosing a miniature transponder clip comprising an RFID tag to small sized devices while taking into consideration operational constraints such as availability of small space, autoclavability of the RFID tag, distortion of RF field in proximity to a metallic object.

It is another object of the present invention to provide a low cost miniature transponder clip comprising a UHF passive RFID tag and an encapsulation module that facilitates longer range of auto-identification, much reduced dependence on the angle & orientation of reading and significantly larger throughput that accrues to using UHF tag method in particular when the RFID tag is attached to physically small & metallic devices thus preventing inadvertent loss of these devices.

Yet another objective of the present invention is to provide a convenient method for automatic deactivation or "killing" the transponder clip on detachment before the small sized device such as a medical implant is used.

SUMMARY OF THE INVENTION

The present application is related to a unique transponder clip comprising a UHF passive RFID tag, an encapsulation module and method of attaching the encapsulation module enclosing the transponder clip to small sized devices. In an aspect, the small sized device may be a small sized medical device such as bone screw, spine screw implants. The transponder clip described herein is enclosed in an encapsulation module that is then attached to a small sized device thereby facilitating auto-identification and tracking of the small sized device.

In an embodiment, a transponder clip may be provided that consists of an RFID transponder IC bonded on a small printed circuit board (PCB). The RFID transponder IC may be a low cost UHF passive RFID tag. A pair of antenna traces (501) is embedded on two edges of the printed circuit board (PCB). In an aspect, the pair of antenna traces (501) may be made up of a conductive metal such as copper. In another aspect, the printed circuit board may be made up of a paper like thin substrate.

In an embodiment, the encapsulation module adapted to enclose transponder clip may consist of a top caddy and a base receptacle. The top caddy is adapted to be adjustably fixed over the base receptacle by employing a fitting mechanism such as snap fit mechanism. The base receptacle may include a cavity for accepting the transponder clip. Further, the base receptacle may include a single notch for unique positioning of the transponder clip. In an aspect, the encapsulation module may enable the transponder clip including the RFID tag to be sterilized or autoclaved along with the small sized device. The base receptacle also includes a pair of special leg fixtures and at least one extended leg fixture. The pair of special leg fixtures and the extended leg fixture includes a cavity at their respective lateral surfaces. The special leg fixtures may be hollow and may have a cavity across their length. The pair of special leg fixtures and the extended leg fixture may be diametrically opposite to each other and provided at the bottom of the base receptacle. In an embodiment, the encapsulation module may be made up of medical plastic such as Radel-R, PCTFE, and the like. A pair of embedded metallic strips is provided that may be embedded directly into the base receptacle. One end of the metallic strips may be exposed at the cavity in the transponder receiving part of the base receptacle and thereon extend through the hollow space provided in the special leg fixtures. The embedded metallic strips extending through the hollow space provided in the pair of special leg fixtures may run within the encapsulation module in a given pattern and may get exposed minimally at the end of the special leg fixtures. In an aspect, the embedded metallic strips may get minimally exposed at the lateral surface towards the end of the special leg fixtures such that the exposed parts face each other. In an aspect, the embedded metallic strip may be made up of an electricity conducting metal such as titanium or copper. The embedded metallic strips may facilitate as antenna trace thereby enabling the RFID tag operation and improve RFID tag performance due to its extended length. In an aspect, the embedded metallic strips enable the transponder clip enclosed in the encapsulation module to be functional even in the proximity of metal taking into consideration the distortion of RF field in the proximity of metal. In another aspect, the embedded metallic strips reduce the dependence on the angle and orientation of reading the transponder clip enclosed in the encapsulation module to be read by the RFI reader.

In another related embodiment, the encapsulation module may include a wire harness. Such a wire harness may pass through the cavities provided in the lateral surfaces of the pair of special leg fixtures and the extended leg fixture. The wire harness may tightly hold a small sized device between the pair of special leg fixtures and the extended leg fixture. Further, the wire harness pulls the individual special leg fixtures towards each other thereby getting the metallic strip extended across the hollow space provided in the pair of special leg fixtures in contact with each other. In another aspect, the wire harness may enable deactivating or auto-killing of the RFID tag when the encapsulation module is removed from the small sized device thereby breaking the wire harness and deactivating the RFID tag.

A method is provided for enclosing the transponder clip in the encapsulation module, and activating as well as deactivating the transponder clip. In an embodiment, the unique miniature transponder clip may be manually fitted on the exposed portions of the metallic strips at the base receptacle. In an aspect, the transponder clip may not be physically bonded with the exposed portions of the metallic strips using a technique such as soldering. The transponder clip may get electrical connection to the metallic strips by parasitic capacitive coupling. The length, width & orientation of the pair of metallic strips may facilitate a greater distance of reading the REID tag of the transponder clip. In an aspect, the RFID tag of the transponder clip may be read by an RFID reader even at a distance of greater than 8 inches. Further, the transponder clip may be activated when the wire harness passing through the cavities of the pair of special leg fixtures and the extended leg fixture pulls the pair of special leg fixtures towards each other thereby electrically coupling the exposed end of the metallic strips facing each other and thus completing the circuit. The transponder clip may be deactivated by cutting or breaking the wire harness thereby releasing the pair of special leg fixtures in their original parallel position that uncouples the exposed end of the metallic strips and breaks the circuit.

BRIEF DESCRIPTION OF DRAWINGS

The foregoing summary, as well as the following detailed description of preferred embodiments, is better understood when read in conjunction with the appended drawings. For the purpose of illustrating the invention, there is shown in the present document example constructions of the invention; however, the invention is not limited to the specific methods and apparatus disclosed in the document and the drawing.

DETAILED DESCRIPTION OF THE INVENTION

Some embodiments of this invention, illustrating its features, will now be discussed:

The present invention provides a transponder clip including a miniature passive RFID transponder IC and a special design antenna on a thin Printed Circuit Board for auto-identification and tracking small sized devices/assets. An encapsulation module is provided for holding the transponder clip and also adapted to be attached to a small sized device or instrument. Further, a related method is also provided for attaching the encapsulation module holding the transponder clip to the small sized device and also for activating and deactivating the transponder clip.

The present invention also gives a feature to improve the performance of the transponder clip by providing a pair of elongated metallic strips from the base of the encapsulation module. The encapsulation module enables the transponder clip to be autoclaved as the clip is enclosed in the encapsulation module. An automatic "killing" or deactivation mechanism is also provided when the encapsulation module is removed from device.

According to the present invention, a transponder clip is embedded inside a special purpose encapsulation module, which is attached to a small sized device. While designing of encapsulation module the physical and operational orientation factors such as space, auto-cleavability of attachment, effect of RF field due to proximity of metal, and the like are taken into consideration. Moreover, the encapsulation module described in the present application enables longer range of auto-identification and reduces the dependence on the angle & orientation of transponder clip reading. The encapsulation module also significantly enhances the throughput particularly when attached to a physically small & metallic device such as bone screw, spine screw, and the like, it results in major benefit in circumventing inadvertent loss of these devices.

Figure 1:
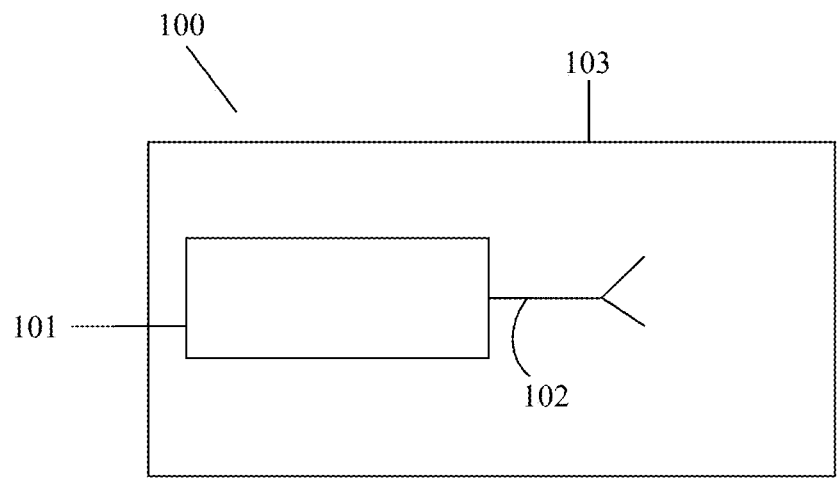
FIG. 1 illustrates the components of the miniature transponder clip according to an embodiment.
Figure 5:
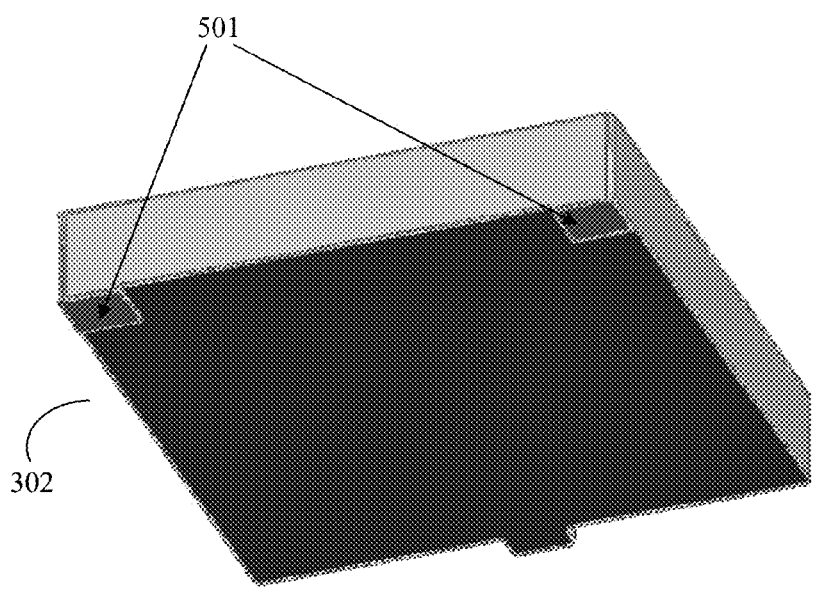
FIG. 5 is a bottom view of the transponder clip according to an embodiment.

FIG. 1 illustrates a miniature transponder clip (100) according to an embodiment of the present invention. The transponder clip (100) includes an RFID transponder IC (101), a small antenna (102) and a printed circuit board (103). RFID transponder IC (101) is bonded on the printed circuit board (103) preferably without any antenna pattern. In an embodiment, the small antenna (102) may be designed as a pair of copper traces on two edges of the printed circuit board (103) by implementing a pair of antenna traces (501) as shown in FIG. 5. In an aspect, the RFID transponder IC (101) may be a UHF passive RFID tag. In another aspect, the printed circuit board (103) may be made of substrate including but not limited to paper type substrate, a plastic type substrate, and the like. In an aspect the RFID transponder IC (101) may be a miniature RFID tag with dimensions less than 10 mm×10 mm. The transponder clip (100) may be provided with a single notch for orientation fixation.

Figure 2:
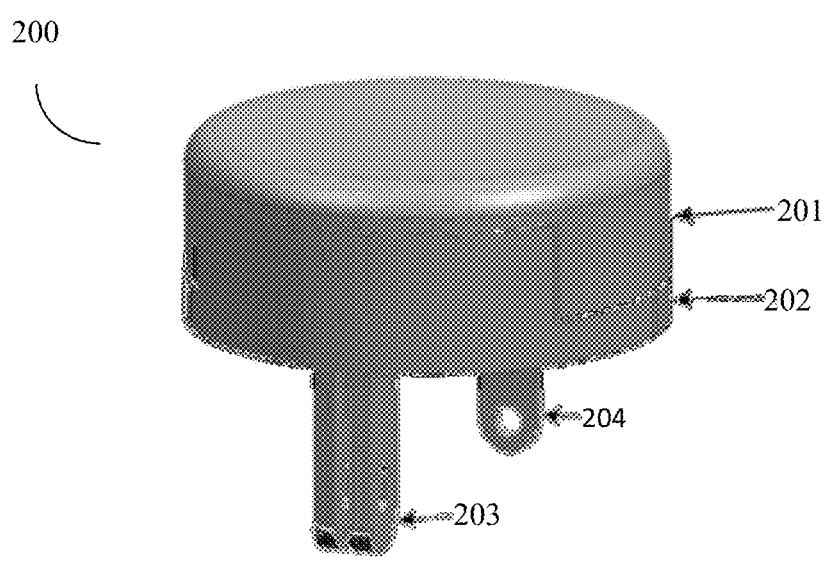
FIG. 2 illustrates the encapsulation module enclosing the transponder clip in accordance with an embodiment of the present invention.

FIG. 2 illustrates an encapsulation module (200). The encapsulation module (200) broadly includes a top caddy (201), a base receptacle (202), a pair of special leg fixtures (203), and at least one support leg fixture (204). In an embodiment, the encapsulation module (200) may be made up of medical plastic such as Radel-R, PCTFE, and the like. In another embodiment, the encapsulation module (200) may be made up of radio-transparent material. The top caddy (201) is adapted to be adjustably fixed over the base receptacle (202) by employing a fitting mechanism such as snap fit mechanism. Further, the base receptacle (202) may include a cavity for accepting the transponder clip (100). The transponder clip (100) may be fitted in the base receptacle (202) of the encapsulation module (200) and the top caddy (201) is then fitted on top of the base receptacle (202). In an embodiment, the encapsulation module (200) may utilize a snaps-fit mechanism for fitting the top caddy (201) into the base receptacle (202). In an aspect, the fitting mechanism utilized by the encapsulation module (200) may facilitate a vacuum environment to the RFID tag enclosed between the top caddy (201) and base receptacle (202) hence providing an autoclavability condition along with environmental protection to the enclosed RFID tag. In another embodiment, a rubber casket may additionally be provided at the bottom of the top caddy (201) that may enable the transponder clip to be fixed between the top caddy and the base receptacle.

The pair of special leg fixtures (203) and support leg fixture (204) enables attaching the encapsulation module (200) over a small sized device. In an embodiment, the pair of special leg fixtures (203) and support leg fixture (204) may include a hole each on the leg fixtures preferably on the lateral surface for incorporating a wire harness through said holes. In another embodiment, the small sized device may be a small sized medical device such as an implant. In an aspect, the small sized medical device may be a bone implant screw, spine implant screw, and the like.

Figure 3:
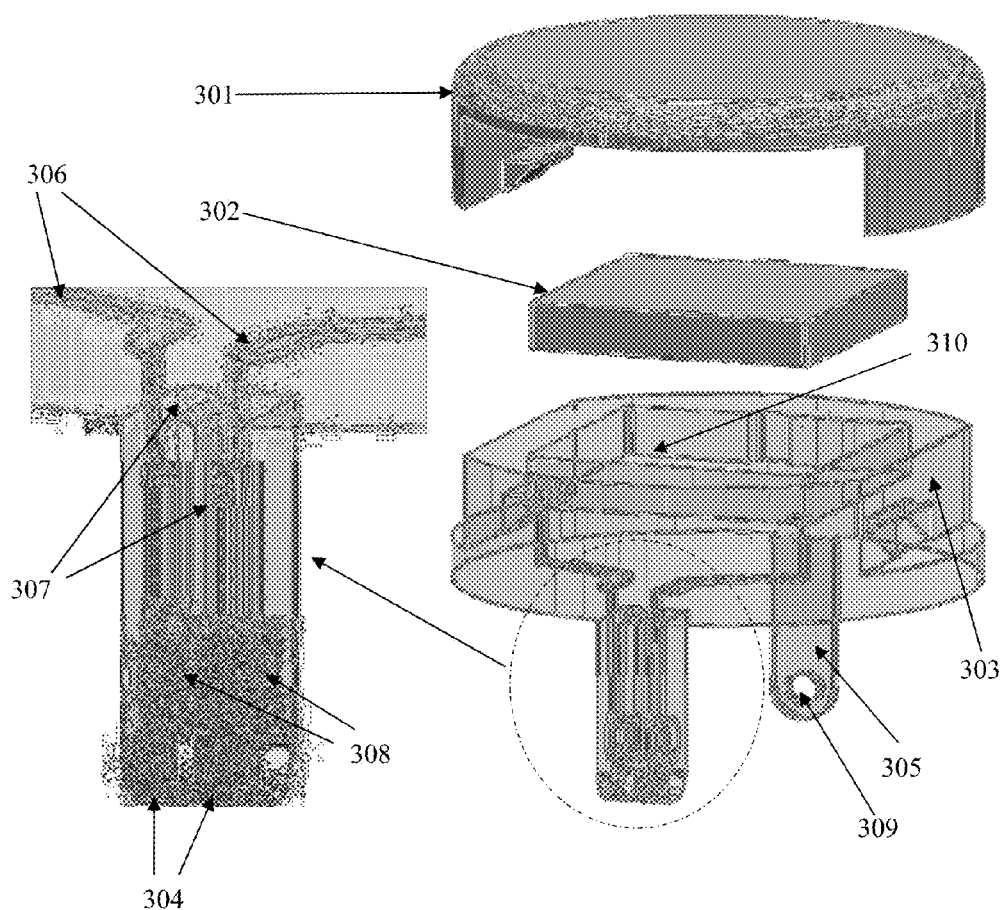
FIG. 3 illustrates an exploded view of the encapsulation module enclosing the transponder clip.

FIG. 3 illustrates an exploded view of the encapsulation module enclosing the transponder clip in accordance with an embodiment. The top caddy (301) is adapted to be attached to the base receptacle (303) by using a snap fit mechanism such as annular snap fit, cantilever snap fit, or torsional snap fit. In the present embodiment, a pair of protruding cantilever snaps is provided in the top caddy (301) and a pair of respective cavities in the base receptacle (303). Further, the transponder clip (302) is provided a single notch and the base receptacle (303) may include a single cavity (310) that may be adapted to accept the notch provided in the transponder clip (100) thereby enabling the transponder clip to be uniquely fitted in the encapsulation module. A pair of special leg fixtures (304) and a support leg fixture (305) is provided for attaching the encapsulation module over a small sized device. The pair of special leg fixtures (304) includes first holes (308) and the support leg fixture (305) includes a cavity second hole (309) at their respective lateral surfaces. Further, the special leg fixtures are hollow and have a cavity (307) across their length. The pair of special leg fixtures (304) and the support leg fixture (305) are diametrically opposite to each other and provided at the bottom of the base receptacle (303). A pair of embedded metallic strips (306) is provided that may be embedded directly into the base receptacle (303). One end of the metallic strips (306) is exposed at the cavity in the transponder receiving part of the base receptacle. The pair of metallic strips (306) extends through the cavity (307) provided in the special leg fixtures. The embedded metallic strips (306) extending through the cavity (307) provided in the pair of special leg fixtures may run within the encapsulation module in a given pattern and gets exposed minimally at the end of the special leg fixtures. In an aspect, the embedded metallic strips may get minimally exposed at the lateral surface towards the end of the special leg fixtures such that the exposed parts face each other. In another aspect, the embedded metallic strip may be made up of an electricity conducting metal such as titanium or copper. The embedded metallic strips may facilitate as antenna trace thereby enabling the RFID tag operation and improve RFID tag performance due to its extended length. In an aspect, the embedded metallic strips enable the transponder clip enclosed in the encapsulation module to be functional even in the proximity of metal taking into consideration the distortion of RF field in the proximity of metal. In another aspect, the embedded metallic strips reduce the dependence on the angle and orientation of reading the transponder clip enclosed in the encapsulation module to be read by the RFI reader.

Figure 6:
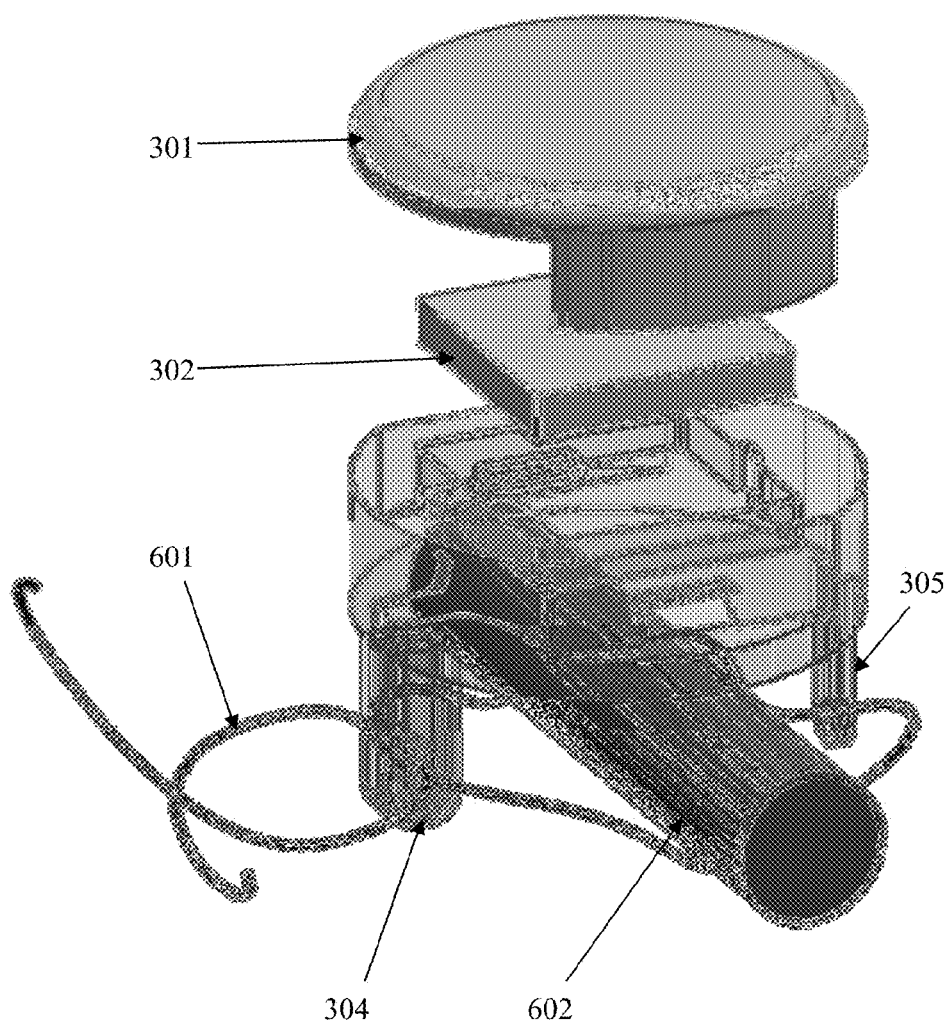
FIG. 6 illustrates an exploded view of the encapsulation module having a wire harness and enclosing the transponder clip.

Once the transponder clip (302) is packaged inside the encapsulation module, the transponder may be made operational only by a wire harness (601 as shown in FIG. 6). The wire harness (601) tightly holds a small sized device (602) between the pair of special leg fixtures (304) and a support leg fixture (305). Further, the wire harness pulls the individual special leg fixtures (304) towards each other thereby getting the metallic strip extended across the cavity (307) provided in the pair of special leg fixtures in contact with each other. In another aspect, the wire harness (601) may enable deactivating or auto-killing of the transponder clip (302) when the encapsulation module is removed from the small sized device thereby breaking the wire harness (601) and deactivating the transponder clip (302).

Figure 4:
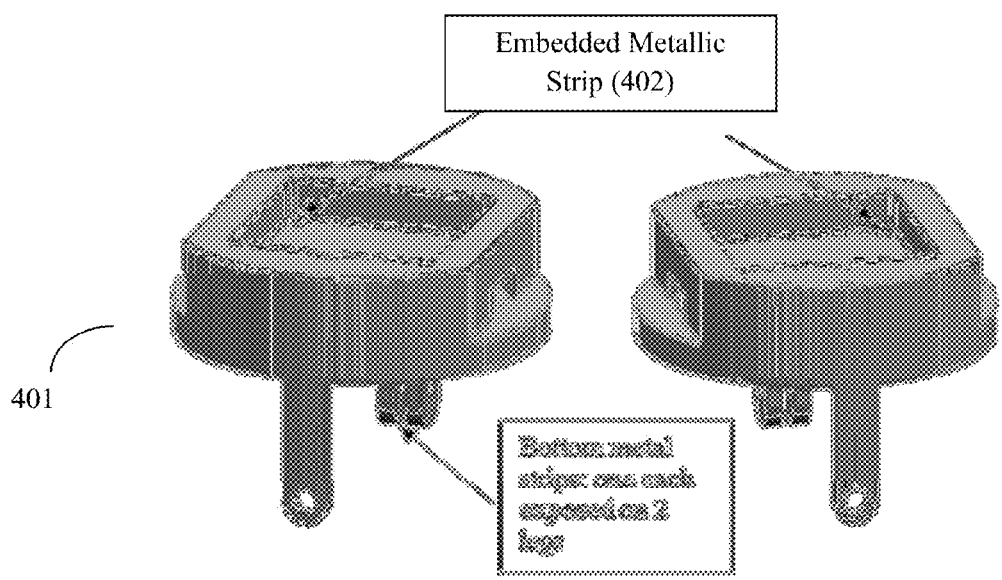
FIG. 4 illustrates the combination of two sub parts with critical feature of the encapsulation module.

FIG. 4 illustrates an embodiment of the present invention wherein the embedded metallic strips (402) is embedded in the bottom corners of the base receptacle (401). One individual embedded metallic strip may be exposed on each of the proximity leg fixtures. The embedded metallic strip may run through the hollow space provided in the pair of special leg fixtures. In an embodiment, each leg may run separate embedded metallic strip from two corners of the base receptacle (401). In a related embodiment, the embedded metallic strip may facilitate improved RFID tag performance due to its extended length especially in the proximity of a metal body thereby overcoming any distortion to the RF field in the proximity of the metal body.

The illustrations of arrangements described herein are intended to provide a general understanding of the structure of various embodiments, and they are not intended to serve as a complete description of all the elements and features of apparatus and systems that might make use of the structures described herein. Many other arrangements will be apparent to those of skill in the art upon reviewing the above description. Other arrangements may be utilized and derived there from, such that structural and logical substitutions and changes may be made without departing from the scope of this disclosure. Figures are also merely representational and may not be drawn to scale. Certain proportions thereof may be exaggerated, while others may be minimized.

Accordingly, the specification and drawings are to be regarded in an illustrative rather than a restrictive sense.

The preceding description has been presented with reference to various embodiments. Persons skilled in the art and technology to which this application pertains will appreciate that alterations and changes in the described structures and methods of operation can be practiced without meaningfully departing from the principle, spirit and scope.

We claim:

1. A communication device for identifying and tracking a device, the communication device comprising:
   a transponder clip comprising:
      a radio frequency identification (RFID) transponder Integrated Circuit (IC);
      a printed circuit board;
      a pair of antenna traces embedded in two edges of the printed circuit board, wherein the RFID transponder IC is electrically coupled with the printed circuit board and with the pair of antenna traces;
   an encapsulation module for encapsulating the transponder clip, wherein the encapsulation module is adapted to be attached to a device to be tracked, the encapsulation module comprising:
      a base receptacle comprising a cavity, wherein the cavity accepts the transponder clip;
      a top caddy adapted to be adjustably fitted over the base receptacle by employing a fitting mechanism;
      at least one support leg fixture coupled to the base receptacle, the at least one support leg fixture having a first hole;
      a pair of special leg fixtures coupled to the base receptacle, wherein each special leg fixture of the pair of special leg fixtures has a second hole, and wherein each special leg fixture of the pair of special leg fixtures has a cavity on a lateral surface thereof, wherein each special leg fixture of the pair of special leg fixtures faces each other;
      a wire harness adapted to be inserted into the first hole and the second hole of each special leg fixture; and
      a pair of metallic strips embedded in the base receptacle;
   wherein an end of each metallic strip of the pair of metallic strips is exposed in the cavity of the base receptacle, wherein the ends of each metallic strip are electrically coupled to the antenna traces of the transponder clip, wherein each metallic strip of the pair of metallic strips extends through the cavity in lateral surfaces of the respective special leg fixture of the pair of special leg fixtures, and wherein each metallic strip of the pair of metallic strips are electrically coupled with each other when the wire harness is fastened to the device through the first hole and the second hole.

2. The communication device as claimed in claim 1, wherein the RFID transponder IC is an Ultra High Frequency (UHF) passive RFID tag.

3. The communication device as claimed in claim 1, wherein the pair of antenna traces is made of a conductive metal selected from at least one of: copper, aluminum, and titanium.

4. The communication device as claimed in claim 1, wherein the printed circuit board is made up of a thin substrate.

5. The communication device as claimed in claim 1, wherein the encapsulation module is made up of medical plastic selected from at least one of Radel-R and Polychlorotrifluoroethylene (PCTFE).

6. The communication device as claimed in claim 1, wherein the top caddy is adapted to be adjustably fixed over the base receptacle by employing a snap fit mechanism.

7. The communication device as claimed in claim 1, wherein the transponder clip is a radio frequency identification (RFID) tag.

8. The communication device as claimed in claim 1, wherein the transponder clip includes a single notch and the base receptacle includes a notch cavity for unique positioning of the transponder clip in the encapsulation module.

9. The communication device as claimed in claim 1, wherein the pair of special leg fixtures, and the at least one support leg fixture are diametrically opposite to each other.

10. The communication device as claimed in claim 1, wherein at least one of the pair of metallic strips is an electricity conducting metal selected from a group of titanium or copper.

11. The communication device as claimed in claim 1, wherein the pair of metallic strips is minimally exposed at a lateral surface towards the distal end of the special leg fixtures such that each metallic strip of the pair of metallic strips face each other.

12. A method comprising:
   embedding a pair of antenna traces in two edges of a printed circuit board;
   electrically coupling a radio frequency identification transponder Integrated Circuit (IC) with the printed circuit board and the pair of antenna traces to form a transponder clip for identifying and tracking a device;
   fitting the transponder clip in a base receptacle such that the pair of antenna traces of the transponder clip are electrically coupled with a minimally exposed proximal end of a pair of metallic strips, wherein the minimally exposed proximal end is embedded in the base receptacle;
   fitting a top caddy over the base receptacle by employing a fitting mechanism; and
   fastening a wire harness to the device, wherein the wire harness is fastened by passing the wire harness through a first hole provided at a distal end of a support leg fixture and a second hole of each special leg fixture of a pair of special leg fixtures such that the wire harness electrically couples a minimally exposed distal end of the pair of metallic strips, thereby activating the transponder clip.

13. The method as claimed in claim 12, further comprising deactivating the transponder clip by unfastening the wire harness such that the minimally exposed distal end of the pair of metallic strips are decoupled.

* * * * *